United States Patent
Aguila et al.

(10) Patent No.: US 10,252,962 B2
(45) Date of Patent: Apr. 9, 2019

(54) PROCESS FOR PRODUCTION OF D-SORBITOL

(71) Applicant: DSM IP ASSETS B.V., Heerlen (NL)

(72) Inventors: Mae Joanne Aguila, Kaiseraugst (CH); Hans Peter Hohmann, Kaiseraugst (CH); Laurent Lefort, Kaiseraugst (CH); Jonathan Alan Medlock, Kaiseraugst (CH); Guenter Pappenberger, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/742,177

(22) PCT Filed: Jul. 14, 2016

(86) PCT No.: PCT/EP2016/066712
§ 371 (c)(1),
(2) Date: Jan. 5, 2018

(87) PCT Pub. No.: WO2017/009404
PCT Pub. Date: Jan. 19, 2017

(65) Prior Publication Data
US 2018/0201558 A1    Jul. 19, 2018

(30) Foreign Application Priority Data
Jul. 14, 2015 (EP) ................... 15176657

(51) Int. Cl.
| C07C 29/149 | (2006.01) |
| B01J 31/24 | (2006.01) |
| B01J 31/18 | (2006.01) |
| B01J 31/20 | (2006.01) |
| C07C 31/26 | (2006.01) |

(52) U.S. Cl.
CPC ........... *C07C 29/149* (2013.01); *B01J 31/181* (2013.01); *B01J 31/189* (2013.01); *B01J 31/20* (2013.01); *B01J 31/2409* (2013.01); *B01J 31/2414* (2013.01); *B01J 31/2452* (2013.01); *B01J 2231/48* (2013.01); *B01J 2531/821* (2013.01); *B01J 2531/827* (2013.01); *C07B 2200/07* (2013.01)

(58) Field of Classification Search
CPC .. C07C 29/149; C07B 2200/07; B01J 31/181; B01J 31/2409; B01J 31/189; B01J 31/2452; B01J 31/20; B01J 31/2414; B01J 2531/821; B01J 2231/48; B01J 2531/827
See application file for complete search history.

(56) References Cited

FOREIGN PATENT DOCUMENTS

GB    1 580 665    12/1980

OTHER PUBLICATIONS

Fabre et al., Hydrogenation of gluconolactones in equilibrium with gluconic acid on Ru (Catalysis Letters 68 (2000)41-44) in view of Doucet et al (Angew. Chem. Ind. Ed. 1998, 37, No. 12, 1703-1707).*
Doucet et al., trans [RuCl2(phonsphane)2(1,2-diamine)] (Angew. Chem. Ind. Ed. 1998, 37, No. 12, 1703-1707).*
Zhang et al., Efficient conversion of D-glucose into D-sorbitol over MCM-41 supported Ru, Carbohydrate Research 346 (2011) 1327-1332.*
International Search Report of PCT/EP2016/066712, dated Sep. 27, 2016, 4 pages.
Written Opinion of the ISA of PCT/EP2016/066712, dated Sep. 27, 2016, 5 pages.
Fabre et al.,"Hydrogenation of Gluconolactones in Equilibrium With Gluconic Acid on Ruthenium Catalyst", Catalysis Letters, Aug. 1, 2000, pp. 41-44.
Rajagopal et al. "Ruc12(Pph3),—Catalyzed Transfer Hydrogenation of D-Glucose", Journal of Molecular Catalysis, Jan. 1, 1992, pp. 199-208.

* cited by examiner

*Primary Examiner* — Jafar F Parsa
(74) *Attorney, Agent, or Firm* — Nixon & Vanderhye P.C.

(57) ABSTRACT

The present invention relates to a new process for the production of D-sorbitol.

20 Claims, No Drawings

PROCESS FOR PRODUCTION OF D-SORBITOL

This application is the U.S. national phase of International Application No. PCT/EP2016/066712 filed Jul. 14, 2016, which designated the U.S. and claims priority to EP Patent Application No. 15176657.3 filed Jul. 14, 2015, the entire contents of each of which are hereby incorporated by reference.

The present invention relates to a new process for the production of sorbitol.

D-Sorbitol, also known as D-glucitol, is a sugar alcohol with a sweet taste which the human body metabolizes slowly.

D-Sorbitol, which IUPAC name is (2S,3R,4R,5R)-hexane-1,2,3,4,5,6-hexol), is the compound of formula (II). In below text, it is referred to as sorbitol.

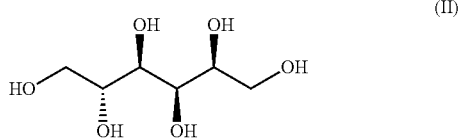 [SMILES: OC[C@@H](O)[C@@H](O)[C@H](O)[C@@H](O)CO]

(II)

Sorbitol is a sugar substitute. It may be listed under the inactive ingredients listed for some foods and products. Its INS number and E number is 420. Sorbitol has approximately 60% the sweetness of sucrose. Furthermore sorbitol is used as a laxative, as well as for example as thickener or humectant in cosmetic applications.

Sorbitol is also used in the so called "sugar-free" chewing gums.

Furthermore sorbitol is also an intermediate in the production of L-ascorbic acid (vitamin C).

Due to the fact that sorbitol can be used in many various applications, there is always a need for new and improved ways of its production.

Nowadays, most sorbitol is made from corn syrup, but it is also found in apples, pears, peaches, and prunes.

Surprisingly we have found a new and improved way to produce sorbitol.

It was found that D-glucono-1,5-lactone can be used as a starting material in a transition metal-based catalyzed hydrogenation to form sorbitol in very high yields.

D-Glucono-1,5-lactone, also known as D-glucono-delta-lactone, IUPAC name: (3R,4S,5S,6R)-3,4,5-trihydroxy-6-(hydroxymethyl)tetrahydro-2H-pyran-2-one), is the compound of formula (I). In below text, it is referred to as gluconolactone.

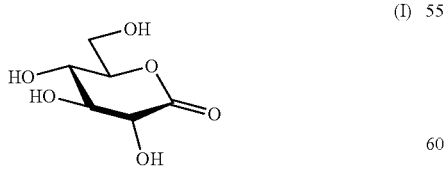

(I)

Gluconolactone is very well known and used compound.

It is a food additive with the E number E575 used as a sequestrant, an acidifier, or a curing, pickling, or leavening agent. Pure gluconolactone is a white odorless crystalline powder.

Gluconolactone can be produced for example by oxidation of D-glucose in the presence of glucose oxidase.

Gluconolactone can also be bought commercially.

Therefore, the present invention relates to a process (P) of production of sorbitol (compound of formula (II)), wherein gluconolactone (compound of formula (I)) is hydrogenated in the presence of at least one transition metal-based complex.

The process according to the present invention, which is a hydrogenation, is carried out in the presence of at least one transition metal-based complex.

Preferred complexes are those wherein the transition metal is chosen from the group consisting of Ru, Ir, Pd, Pt, Rh, Fe, Os, Ni and Co, more preferably Ru and Ir. More preferably, complexes are those wherein the transition metal is chosen from the group consisting of Ru and Ir and which comprise at least one organic ligand. Very preferred complexes are those wherein the transition metal is ruthenium and which comprise at least one organic ligand containing at least on nitrogen donor.

Especially preferred complexes are those wherein the transition metal is ruthenium and which comprise at least one ligand, wherein the ligand contains at least one nitrogen and one phosphorus donor or the ligand contains at least one nitrogen and one carbene-type donor.

Also especially preferred complexes are those wherein the transition metal is iridium, and which comprise at least one ligand, wherein the ligand contains at least one nitrogen donor.

Some very preferred Ru and Ir complexes are those of the following formula (III) (VIII):

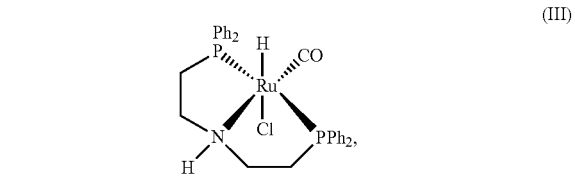

(III)

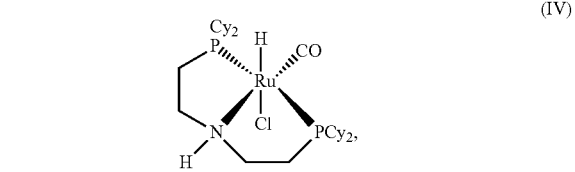

(IV)

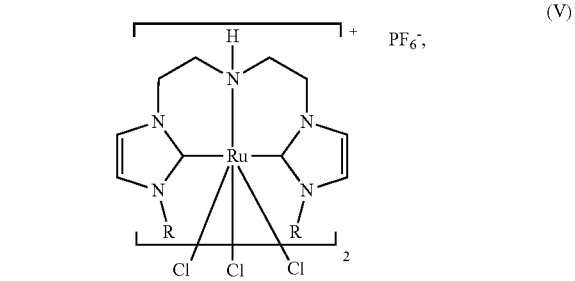

(V)

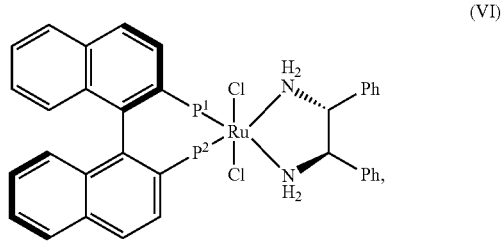

(VI)

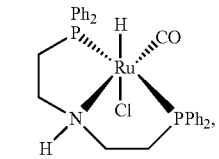

(III)

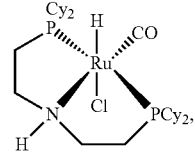

(IV)

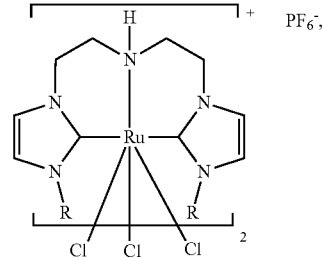

(V)

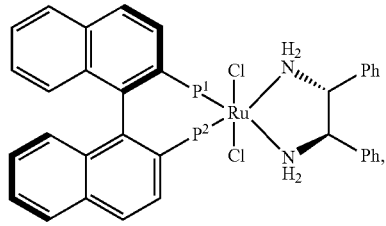

(VI)

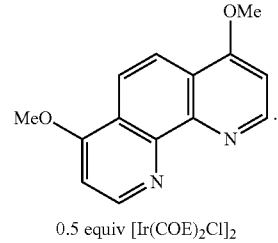

HBr and 0.5 equiv [Ir(COE)₂Cl]₂
Ir-bisNHC, R = Mes (VII)

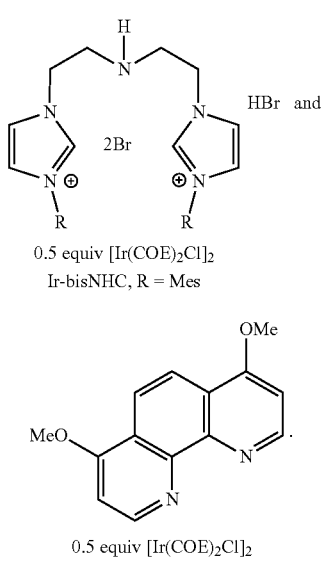

0.5 equiv [Ir(COE)₂Cl]₂

(VIII)

All these preferred complexes of formula (III)-(VIII) are known and can either be purchased from commercial sources (i.e. from STREM Chemicals Inc. or Sigma-Aldrich Chemicals) or can they be produced according to the prior art (as described in Angew. Chem. Int. Ed., 1998, 37, 1703; or Org. Process Res. Rew., 2012, 16, 166).

The catalysts can be pre-formed from a metal precursor and at least one organic ligand, or the desired metal complex can be formed in situ.

Therefore, the present invention also relates to a process (P1), which is process (P), wherein the transition metal of the transition metal based complex is selected from the group consisting of Ru, Ir, Pd, Pt, Rh, Fe, Os, Ni and Co.

Therefore, the present invention also relates to a process (P2), which is process (P), wherein the transition metal of the transition metal based complex is selected from the group consisting of Ru and Ir.

Therefore, the present invention also relates to a process (P3), which is process (P2), wherein the transition metal based complex comprises at least one organic ligand.

Therefore, the present invention also relates to a process (P4), which is process (P), wherein the Ru based complex comprises at least one organic ligand containing at least one nitrogen donor.

Therefore, the present invention also relates to a process (P4'), which is process (P), wherein the Ru based complex comprises at least one organic ligand, wherein the ligand contains at least one nitrogen and one phosphorus donor.

Therefore, the present invention also relates to a process (P4"), which is process (P), wherein the Ru based complex comprises at least one organic ligand, wherein the ligand contains at least one nitrogen and one carbene-type donor.

Therefore, the present invention also relates to a process (P5), which is process (P), wherein the Ir based complex comprises at least one ligand, wherein the ligand contains at least one nitrogen donor.

Therefore, the present invention also relates to a process (P6), which is process (P), (P1), (P2), (P3), (P4), (P4'), (P4") or (P5), wherein transition metal based complex is selected from the group consisting of the complexes shown in formulae (III) (VIII):

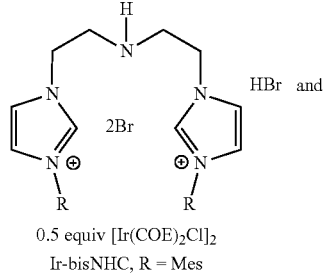

(VII)

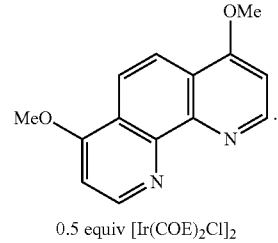

0.5 equiv [Ir(COE)₂Cl]₂
Ir-bisNHC, R = Mes (VIII)

0.5 equiv [Ir(COE)₂Cl]₂

The process according to the present invention is catalyzed homogeneously.

The process according to the present invention is usually carried out in a solvent or a mixture of solvents.

Suitable solvents are non-aqueous, organic, polar solvents, such as alcohols (e.g. methanol, ethanol, propanol), ethers (e.g. THF) or amides.

Therefore, the present invention also relates to a process (P7), which is process (P), (P1), (P2), (P3), (P4), (P4'), (P4"), (P5) or (P6), wherein the process is carried out in at least one solvent.

Therefore, the present invention also relates to a process (P7'), which is process (P7), wherein the solvent is (or the solvents are) selected from a non-aqueous, organic or polar solvent(s).

Therefore, the present invention also relates to a process (P7"), which is process (P7) or (P7'), wherein the solvent is selected from the group consisting of alcohols (e.g. methanol, ethanol, propanol), ethers (e.g. THF) and amides.

Therefore, the present invention also relates to a process (P7"'), which is process (P7), (P7') or (P7"), wherein the solvent is selected from alcohols.

The hydrogenation according to the present invention is usually carried out with $H_2$ gas. Preferably, the hydrogenation according to the present invention is carried out under pressure. The pressure (by the $H_2$ gas) is usually at least about 2 bar. It can go up to about 200 bar. Thus, in a preferred embodiment the pressure is in the range of from about 2 to about 200 bar, more preferably from about 5 to about 100 bar, even more preferably from about 10 to about 60 bar.

Therefore, the present invention also relates to a process (P8), which is process (P), (P1), (P2), (P3), (P4), (P4'), (P4"), (P5), (P6), (P7), (P7'), (P7") or (P7"'), wherein the process is carried out with $H_2$ gas.

Therefore, the present invention also relates to a process (P9), which is process (P), (P1), (P2), (P3), (P4), (P4'), (P4"), (P5), (P6), (P7), (P7'), (P7"), (P7"') or (P8), wherein the process is carried out under pressure.

The process according to the present invention is usually carried out at elevated temperature. The term "elevated temperature" includes but is not limited to temperature which is above room temperature, e.g. at least 25° C. and above (typically a temperature of at least 30° C. to 40° C.). A preferred temperature range is from about 20° C. to about 150° C., more preferably from about 30° C. to about 100° C.

Therefore, the present invention also relates to a process (P10), which is process (P), (P1), (P2), (P3), (P4), (P4'), (P4"), (P5), (P6), (P7), (P7'), (P7"), (P7"'), (P8), (P9) or (P9'), wherein the process is carried out at an elevated temperature.

Therefore, the present invention also relates to a process (P10'), which is process (P10), wherein the process is carried at a temperature range from about 20° C. to about 150° C., preferably from about 30° C. to about 100° C.

The process according to the present invention is usually carried out at a molar substrate to catalyst ratio (S/C ratio) of about 50 to about 100000, preferably about 100 to about 40000, more preferably about 5000 to about 30000.

Therefore, the present invention also relates to a process (P11), which is process (P), (P1), (P2), (P3), (P4), (P4'), (P4"), (P5), (P6), (P7), (P7'), (P7"), (P7"'), (P8), (P9), (P9'), (P10) or (P10'), wherein the process is carried out at a molar substrate to catalyst ratio (S/C ratio) of about 50 to about 100000, preferably about 100 to about 40000, more preferably of about 5000 to about 30000.

The process according the present invention can also be carried out in the presence of at least one base, preferably at least one alkoxide base (i.e. $NaOCH_3$, $KOCH_3$, NaOi-propanol, KOi-propanol, NaOtbutanol, KOtbutanol).

Therefore, the present invention also relates to a process (P12), which is process (P), (P1), (P2), (P3), (P4), (P4'), (P4"), (P5), (P6), (P7), (P7'), (P7"), (P7"'), (P8), (P9), (P9'), (P10), (P10') or (P11), wherein the process is carried out in the presence of at least one base.

Therefore, the present invention also relates to a process (P12'), which is process (P12), wherein the process is carried out in the presence of at least one alkoxide base.

The product of the process according to the present invention [compound of formula (II)] is as stated above obtained in excellent yield, including but not limited to yields in the range of at least 87%, such as e.g. at least 90 or 95%, preferably in the range of at least 98%. The product can be purified (when needed) using commonly known methods.

The invention is illustrated by the following Examples. All temperatures are given in ° C. and all parts and percentages are related to the weight.

EXAMPLE 1: CONVERSION OF GLUCONOLACTONE TO SORBITOL UNDER VARIOUS CONDITIONS

General Procedure for Hydrogenation:

All manipulations were done in a $N_2$-filled glovebox, except for weighing of gluconolactone. In air, gluconolactone samples (1.0 mmol) were weighed into 5-mL crimp vials and transferred in $N_2$-filled glovebox. Into these samples, KOMe solution in methanol (5 mol % wt gluconolactone) and catalyst solution/slurry in methanol (0.5 mol % wt gluconolactone, S/C 200) were added; volume is further diluted to 3.0 mL with methanol. These vials were capped with PTFE coated septum and placed inside a Premex 96er parallel hydrogenation reactor. The system was purged with $N_2$ (3×10 bar) and $H_2$ (3×10 bar). The reactions were carried out 50 bar $H_2$, 70° C. 16 h with stirring (300 rpm). After the reaction, HPLC samples were prepared in deionized $H_2O$. Concentrations of the gluconolactone and sorbitol in the reaction were determined using calibration curves.

Analysis:

Products were analyzed with HPLC using Agilent Technologies 1260 Infinity instrument equipped with Waters 2414 Refractive Index Detector. The parameters are column: BIORAD Aminez-HPX-87H, 300×7.8 mm, column temperature: 50° C., flow rate: 0.55 mL/min, injection volume: 100 μL, eluent: 5 mM $H_2SO_{4(aq)}$, collection time: 60 min. Retention times, min: gluconolactone=9.6, sorbitol=10.9.

TABLE 1

Ru- and Ir-catalyst testing (Conditions: 1 mmol gluconolactone, 5 mol % KOMe, 0.5 mol % catalyst, 3 mL total volume methanol, 50 bar $H_2$, 16 h, HPLC analysis in $H_2O$, DF = 168; $^a$at 70° C., $^b$at 90° C.).

| Catalyst | Gluconolactone [mM] | Sorbitol [mM] | Conversion [%] |
|---|---|---|---|
| III$^a$ | 8.9 | 379 | 98 |
| IV$^a$ | 194 | 165 | 46 |
| V$^b$ | 2.2 | 339 | 99 |
| VI$^b$ | 163 | 153 | 49 |
| VII$^b$ | 146 | 128 | 47 |
| VIII$^b$ | 178 | 136 | 43 |
| None (Ref 1) | 363 | 0 | 0 |

TABLE 2

Solvent testing using III as catalyst (Conditions: 1 mmol gluconolactone, 5 mol % KOMe, 0.5 mol % III, 3 mL total volume, 50 bar $H_2$, at 70° C., 16 h, HPLC analysis in $H_2O$, DF = 168).

| Catalyst | Gluconolactone [mM] | Sorbitol [mM] | Conversion [%] |
|---|---|---|---|
| Methanol | 7.7 | 347 | 98 |
| Ethanol | 18.1 | 388 | 96 |
| Isopropanol | 58.7 | 262 | 82 |
| Tetrahydrofuran | 278 | 58.6 | 18 |

TABLE 3

Variation of the molar substrate-to-catalyst (S/C) ratio using III as catalyst (Conditions: 1 mmol gluconolactone, 5 mol % KOMe, 0.02-0.002 mol % III, 3 mL total volume methanol, 50 bar $H_2$, 90° C., 16 h, HPLC analysis in $H_2O$, DF = 168).

| S/C | Gluconolactone [mM] | Sorbitol [mM] | Conversion [%] |
|---|---|---|---|
| 5000 | 1.1 | 305 | 100 |
| 10000 | 1.7 | 290 | 99 |
| 20000 | 6.0 | 397 | 99 |
| 50000 | 68.8 | 183 | 73 |

TABLE 4

Variation of temperature and amount of base using III as catalyst (Conditions: 1 mmol gluconolactone, 1-5 mol % KOMe, 0.5 mol % III, 3 mL total volume methanol, 50 bar $H_2$, 16 h, HPLC analysis in $H_2O$, DF = 168).

| Conditions | Gluconolactone [mM] | Sorbitol [mM] | Conversion [%] |
|---|---|---|---|
| 5 mol % KOMe, 70° C. | 8.9 | 379 | 98 |
| 1 mol % KOMe, 90° C. | 5.7 | 378 | 99 |

EXAMPLE 2: CONVERSION OF GLUCONOLACTONE TO SORBITOL

In air, gluconolactone (10.0 mmol, 1.8 g) was weighed into a 120-mL high pressure stainless steel reactor (EM60-100-HC, Premex) and transferred in $N_2$-filled glovebox. Into this, 10 mL methanol was added, followed by KOMe (5 mol % wt gluconolactone, 0.5 mmol, 0.035 g) solution in methanol (10 mL) and catalyst III (0.02 mol % wt gluconolactone, S/C 5000) solution/slurry in methanol (10 mL). The reactor was closed inside the glovebox. The autoclave was purged with $N_2$ (5×20 bars) and $H_2$ (5×10 bars). The reaction were carried out at 50 bar $H_2$, 90° C. with stirring (1000 rpm). After the reaction, HPLC samples were prepared in deionized $H_2O$. Concentrations of the gluconolactone and sorbitol in the reaction were determined using calibration curves. The solvent from the reaction mixture was removed in vacuo to obtained a crude yield of sorbitol (1.9 g) from the reaction. The analytical method used was the same as in Example 1 analysis showed 4.9 mM gluconolactone and 356 mM sorbitol (99% conversion).

The invention claimed is:

1. A process for producing a compound of formula (II):

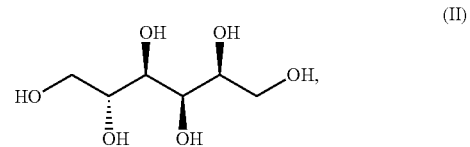

wherein the process comprises hydrogenating a compound of formula (I):

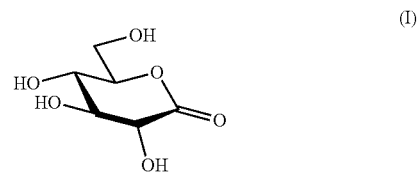

in the presence of at least one transition metal-based complex to obtain the compound of formula (II).

2. The process according to claim 1, wherein the transition metal of the transition metal based complex is selected from the group consisting of Ru, Ir, Pd, Pt, Rh, Fe, Os, Ni, and Co.

3. The process according to claim 2, wherein the transition metal of the transition metal based complex is selected from the group consisting of Ru and Ir.

4. The process according to claim 1, wherein the transition metal based complex comprises at least one organic ligand.

5. The process according to claim 1, wherein the transition metal based complex is selected from the group consisting of the complexes of formulae (III)-(VIII):

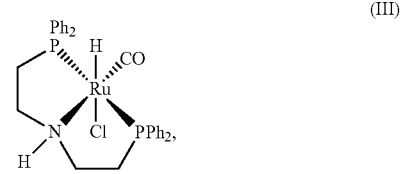

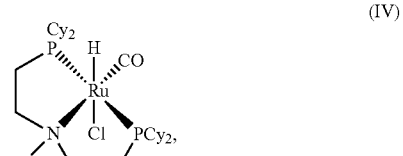

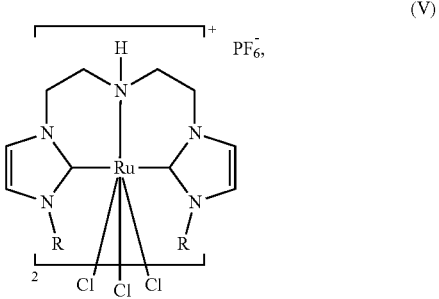

-continued

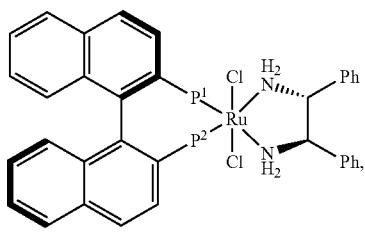
(VI)

0.5 equiv [Ir(COE)$_2$Cl]$_2$

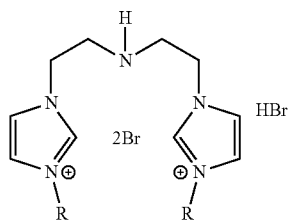
(VII)

Ir-bisNHC, R = Mes    and 0.5 equiv [Ir(COE)$_2$Cl]$_2$

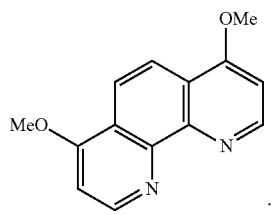
(VIII)

6. The process according to claim 1, wherein the process is carried out in at least one solvent.

7. The process according to claim 6, wherein the process is carried out in at least one non-aqueous, organic or polar solvent.

8. The process according to claim 1, wherein the process is carried out in the presence of H$_2$ gas.

9. The process according to claim 1, wherein the process is carried out at a pressure of about 2 bar to about 200 bar.

10. The process according to claim 1, wherein the process is carried out at a temperature in the range from about 20° C. to about 150° C.

11. The process according to claim 1, wherein the process is carried out at a molar ratio of substrate to catalyst in the range of about 50 to about 100000.

12. The process according to claim 1, wherein the process is carried out in the presence of at least one base.

13. The process according to claim 1, wherein the process is carried out at a pressure of about 5 bar to about 100 bar.

14. The process according to claim 1, wherein the process is carried out at a pressure of about 10 bar to about 60 bar.

15. The process according to claim 1, wherein the process is carried out at a temperature in the range from about 30° C. to about 100° C.

16. The process according to claim 1, wherein the process is carried out at a molar ratio of substrate to catalyst in the range of about 100 to about 40000.

17. The process according to claim 1, wherein the process is carried out at a molar ratio of substrate to catalyst in the range of about 5000 to about 30000.

18. The process according to claim 1, wherein the process is carried out in the presence of at least one alkoxide base.

19. A process for producing a compound of formula (II):

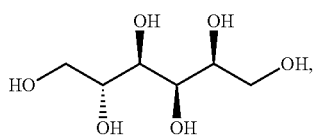
(II)

wherein the process comprises hydrogenating a compound of formula (I):

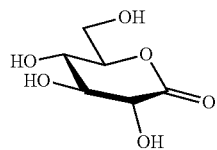
(I)

in the presence of at least one homogenous transition metal-based complex and at least one solvent to obtain the compound of formula (II).

20. The process according to claim 19, wherein the at least one homogenous transition metal-based complex is at least one selected from the group consisting of catalysts according to formulas (III)-(VIII):

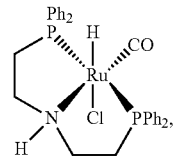
(III)

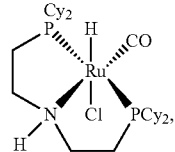
(IV)

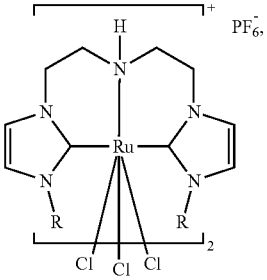
(V)

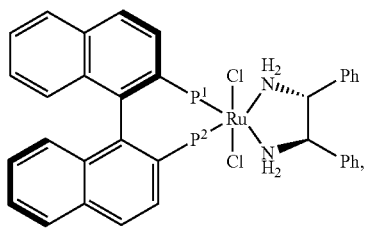
(VI)

-continued
0.5 equiv [Ir(COE)₂Cl]₂
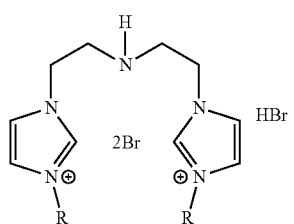
Ir-bisNHC, R = Mes         and
0.5 equiv [Ir(COE)₂Cl]₂
(VII)
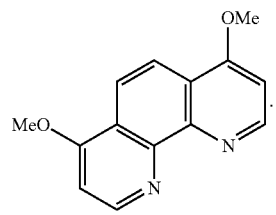
(VIII)
\* \* \* \* \*